US009452419B2

(12) United States Patent
Rizkalla et al.

(10) Patent No.: US 9,452,419 B2
(45) Date of Patent: Sep. 27, 2016

(54) CARRIER FOR ETHYLENE OXIDE CATALYSTS

(71) Applicant: Scientific Design Company, Inc., Little Ferry, NJ (US)

(72) Inventors: Nabil Rizkalla, Rivervale, NJ (US); Andrzej Rokicki, Mountain Lakes, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 121 days.

(21) Appl. No.: 14/279,570

(22) Filed: May 16, 2014

(65) Prior Publication Data

US 2014/0343307 A1 Nov. 20, 2014

Related U.S. Application Data

(60) Provisional application No. 61/824,101, filed on May 16, 2013.

(51) Int. Cl.
| | |
|---|---|
| *B01J 21/06* | (2006.01) |
| *B01J 23/50* | (2006.01) |
| *B01J 23/68* | (2006.01) |
| *C07D 301/10* | (2006.01) |
| *B01J 37/02* | (2006.01) |
| *B01J 23/26* | (2006.01) |

(52) U.S. Cl.
CPC ............... *B01J 23/685* (2013.01); *B01J 23/50* (2013.01); *B01J 23/688* (2013.01); *B01J 37/0207* (2013.01); *C07D 301/10* (2013.01); *B01J 21/063* (2013.01); *B01J 23/26* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,226,782 A | 10/1980 | Hayden et al. | |
| 4,242,235 A | 12/1980 | Cognion et al. | |
| 4,761,394 A | 8/1988 | Lauritzen | |
| 4,766,105 A | 8/1988 | Lauritzen | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,112,795 A | 5/1992 | Minahan et al. | |
| 5,187,140 A | 2/1993 | Thorsteinson et al. | |
| 5,266,548 A | 11/1993 | Koradia et al. | |
| 5,380,697 A | 1/1995 | Matusz et al. | |
| 5,407,888 A | 4/1995 | Herzog et al. | |
| 5,597,773 A | 1/1997 | Evans et al. | |
| 5,831,037 A | 11/1998 | Ohsuga et al. | |
| 6,831,037 B2 | 12/2004 | Szymanski et al. | |
| 2004/0110973 A1 | 6/2004 | Matusz | |
| 2005/0096219 A1 | 5/2005 | Szymanski et al. | |
| 2010/0267969 A1 | 10/2010 | Liu et al. | |
| 2012/0065055 A1 | 3/2012 | Jiang et al. | |
| 2012/0226058 A1 | 9/2012 | Pak et al. | |
| 2013/0006002 A1 | 1/2013 | Rizkalla | |

OTHER PUBLICATIONS

Drake, L.C., et al., "Macropore-Size Distributions in Some Typical Porous Substances", Ind. Eng. Chem. Anal. Ed., Publication Date: Dec. 1945, 17 (12), pp. 787-791.
Brunauer, S., et al., "Adsorption of Gases in Multimolecular Layers", J. Am. Chem. Soc., Feb. 1938, pp. 309-316.
International Search Report and Written Opinion dated Feb. 10, 2015 from related International Application No. PCT/US2014/038019.

*Primary Examiner* — Colin W Slifka

(74) *Attorney, Agent, or Firm* — Scully, Scott, Murphy & Presser, P.C.

(57) ABSTRACT

A carrier for an ethylene epoxidation catalyst is provided that includes an alumina first component and a mixed metal oxide of alumina second component. The mixed metal oxide of alumina second component comprises a corundum lattice structure having a plurality of O—Al—O bonds, wherein an Al atom of at least one O—Al—O bond of the plurality of O—Al—O bonds, but not all of the plurality of O—Al—O bonds, is replaced with a divalent or trivalent transition metal selected from the group consisting of scandium (Sc), titanium (Ti), vanadium (V), chromium (Cr), manganese (Mn), iron (Fe), cobalt (Co), nickel (Ni) copper (Cu), and zinc (Zn). A catalyst containing the carrier, as well as a process for the epoxidation of ethylene using the catalyst are also disclosed.

43 Claims, No Drawings

CARRIER FOR ETHYLENE OXIDE CATALYSTS

CROSS REFERENCE TO RELATED APPLICATION

This application claims benefit of U.S. Provisional Application Ser. No. 61/824,101, filed May 16, 2013, the entire content of which is incorporated herein by reference.

FIELD OF THE INVENTION

The present disclosure relates to silver-based ethylene oxide catalysts, and more particularly, to carriers for such catalysts.

BACKGROUND

As known in the art, high selectivity catalysts (HSCs) for the epoxidation of ethylene refer to those catalysts that possess selectivity values higher than high activity catalysts (HACs) used for the same purpose. Both types of catalysts include silver as the active catalytic component on a refractory support (i.e., carrier). Typically, one or more promoters are included in the catalyst to improve or adjust properties of the catalyst, such as selectivity.

Generally, but not necessarily always, HSCs achieve the higher selectivity (typically, in excess of 87 mole % or above). Typically, one or more additional promoters selected from alkali metals (e.g., cesium), alkaline earth metals, rhenium, transition metals (e.g., tungsten compounds), and main group metals (e.g., sulfur and/or halide compounds) are also included.

There are also ethylene epoxidation catalysts that may not possess the selectivity values typically associated with HSCs, though the selectivity values are improved over HACs. These types of catalysts can also be considered within the class of HSCs, or alternatively, they can be considered to belong to a separate class, e.g., "medium selectivity catalysts" or "MSCs." These types of catalysts typically exhibit selectivities of at least 83 mole % and up to 87 mole %.

It is well known that with extended use of a catalyst, the catalyst will age (i.e., degrade) to a point until use of the catalyst is no longer practical. There is thus a continuous effort to extend the useful lifetime (i.e., "longevity" or "usable life") of catalysts. The useful lifetime of the catalyst is directly dependent on the stability of the catalyst. As used herein, the "useful lifetime" is the time period for which a catalyst can be used until one or more of its functional parameters, such as selectivity or activity, degrade to such a level that use of the catalyst becomes impractical.

Stability of the catalyst has largely been attributed to various characteristics of the carrier. Some characteristics of the carrier that have undergone much research include carrier formulation, surface area, porosity, and pore volume distribution, among others.

The most widely used formulation for the carriers of ethylene epoxidation catalysts are those based on alumina, typically c'-alumina. Much research has been directed to investigating the effect of the alumina composition for improving stability and other properties of the catalyst. The preparation and modification of alumina carriers for enhancing ethylene epoxidation catalyst performance are described, for example, in U.S. Pat. Nos. 4,226,782, 4,242,235, 5,266, 548, 5,380,697, 5,597,773, 5,831,037 and 6,831,037 as well as in U.S. Patent Application Publication Nos. 2004/0110973 A1 and 2005/0096219 A1.

However, there remains a need in the art for further improvements in the stability of ethylene epoxidation catalysts. There is a particular need for improving the stability of such catalysts by modifying the carrier by means that are facile and financially feasible.

SUMMARY

The present disclosure provides alumina carriers useful for preparing silver-based catalysts, such as HSCs and MSCs, having an increased stability. The alumina carriers of the present disclosure comprise alumina, as a first component, and a mixed metal oxide of alumina as a second component. The term "mixed metal oxide of alumina" is used throughout the present disclosure to denote alumina which comprises a corundum lattice structure having a plurality of O—Al—O bonds, wherein an Al atom of at least one O—Al—O bond of the plurality of O—Al—O bonds, but not all of the plurality of O—Al—O bonds, is replaced with a divalent or trivalent transition metal selected from the group consisting of scandium (Sc), titanium (Ti), vanadium (V), chromium (Cr), manganese (Mn), iron (Fe), cobalt (Co), nickel (Ni) copper (Cu), and zinc (Zn) i.e., a transition metal from the first row of the Periodic Table of Elements. In accordance with the present disclosure, this mixed metal oxide of alumina coats most of the surface of the alumina and, in most cases, provides color to a carrier which has an otherwise characteristic pale white appearance.

The above described mixed metal oxide of alumina can be formed during a stage of forming alumina particles from an alumina precursor, during a stage of making the carrier from an alumina powder, or via doping the preformed carrier. In some embodiments, the mixed metal oxide of alumina can be formed during any combination of the above mentioned stages. In any of these stages of forming the carrier, a 'mixed metal oxide of alumina precursor' is employed which interacts with alumina or its precursors and upon firing (i.e., calcination) forms the mixed metal oxide of alumina second component of the carrier.

The present disclosure is also directed to stability-enhanced ethylene epoxidation catalysts. The stability-enhanced ethylene epoxidation catalysts of the present disclosure are silver-based, contain one or more promoters and have a selectivity of about 83 mol % or greater. In one embodiment, the stability-enhanced ethylene epoxidation catalyst comprises the carrier described above, along with a catalytic amount of silver and a promoting amount of rhenium deposited on and/or in the carrier. In another embodiment, a stability-enhanced ethylene epoxidation catalyst is provided that comprises the carrier described above, along with a catalytic amount of silver and a promoting amount of one or more alkali metals deposited on and/or in the carrier. The increased stability results in silver-based catalysts including HSCs and MSCs with longer usable lifetimes, and particularly maintaining the catalyst's activity and high selectivity for an extended period, as compared to such catalysts without a mixed metal oxide of alumina as one of the carrier components, over equivalent time periods of usage.

The present disclosure is also directed to a method for the vapor phase conversion of ethylene to ethylene oxide (EO) in the presence of oxygen, the method comprising reacting a reaction mixture comprising ethylene and oxygen in the presence of one of the stability-enhanced ethylene epoxidation catalysts described above.

The present disclosure provides stability-enhanced ethylene epoxidation catalysts which are advantageously more resistant to degradation and retain a higher level of selectivity over time than similar catalysts that do not contain a mixed metal oxide of alumina as one of the carrier components. The present disclosure is thus highly beneficial in that the longer catalyst life amounts to significant financial savings, greater efficiency of the process, and less process and catalyst waste.

The catalyst of the present disclosure can also exhibit increased crush strength and attrition resistance as compared to an equivalent ethylene oxide catalyst that is present on a carrier which is otherwise identical to the carrier of the present disclosure except that the carrier does not include a mixed metal oxide of alumina component.

DETAILED DESCRIPTION

In one aspect, the present disclosure is directed to an improved alumina carrier for an ethylene epoxidation catalyst. The carrier of the present disclosure comprises alumina as a first component and a mixed metal oxide of alumina as a second component. The carrier is improved in that it imparts an enhanced stability to a silver-based catalyst derived therefrom. By 'enhanced stability' it is meant that the silver-based catalysts supported on the carrier of the present disclosure have longer usable lifetimes, and particularly, a significantly reduced degradation in selectivity as compared to such catalysts supported on a carrier without a mixed metal oxide of alumina component, over equivalent time periods of usage.

Also, the catalysts of the present disclosure that is formed on the carrier of the present disclosure exhibit increased crush strength and attrition resistance as compared to an equivalent ethylene oxide catalyst that is present on a carrier which is otherwise identical to the carrier of the present disclosure except that the carrier does not include the metal oxide of alumina component of the present disclosure.

The carrier (i.e., support) which provides the above improvements includes a mixed oxide of alumina as one of the components of the carrier. The mixed oxide of alumina, which coats most of the surface of the alumina component of the carrier, can be formed during a stage of forming alumina particles from an alumina precursor, during a stage of making the carrier from an alumina powder, or after forming a preformed carrier. In some embodiments, the mixed oxide of alumina can be formed during any combination of the above mentioned stages.

As mentioned above, the term "mixed metal oxide of alumina" denotes alumina which comprises a corundum lattice structure having a plurality of O—Al—O bonds, wherein an Al atom of at least one O—Al—O bond of the plurality of O—Al—O bonds, but not all of the plurality of O—Al— bonds, is replaced with a divalent or trivalent transition metal selected from the group consisting of Sc, Ti, V, Cr, Mn, Fe, Co, Ni, Zn Cu and Zn, i.e., a transition metal from the first row of the Periodic Table of Elements. In some embodiments, the divalent or trivalent transition metal is selected from the group consisting of Cr, Co, Mn, and Ni. In a further embodiment, the divalent or trivalent transition metal is Cr.

In some embodiments of the present disclosure, the mixed metal oxide of alumina can be a spinel. The term "spinel" refers to a class of materials of the general formula $MAl_2O_4$ wherein M can be one of the transition metals mentioned above.

In other embodiments of the present disclosure, the mixed metal oxide of alumina is a solid state solution of one or more of the divalent or trivalent transition metals in the corundum lattice structure of alumina. In such an embodiment, the mixed metal oxide is considered a solution rather than a compound since the lattice structure of the alumina remains unchanged by addition of the divalent or trivalent transition metals.

In some embodiments of the present disclosure, some portions of the O—Al—O bonds within the corundum lattice structure, but not all, are replaced with a divalent or trivalent first transition metal selected from the group consisting of Ti, V, Cr, Mn, Fe, Co, Ni, Zn Cu and Zn, while other portions of the O—Al—O bonds within the corundum lattice structure, but not all, are replaced with a divalent or trivalent second transition metal selected from the group consisting of Ti, V, Cr, Mn, Fe, Co, Ni, Zn Cu and Zn which differs from the first transition metal.

The mixed metal oxide of alumina second component of the alumina carrier adds another material to the alumina carrier (oxide phase) which is believed to improve the strength and microstructure of the alumina carrier as compared to an alumina carrier not including the mixed metal oxide of alumina.

The mixed metal oxide of alumina second component of the alumina carrier is located on a surface of the alumina providing a coating thereto. In one embodiment, the coating of mixed metal oxide of alumina is a continuous coating which covers the entire surface of the carrier as well as the pores of the carrier. In another embodiment, the coating of mixed metal oxide of alumina is a discontinuous coating which may or may not cover all the pores of the carrier. In some embodiments, the mixed metal oxide of alumina can also be located within the pores of the alumina carrier and/or within the bulk of the alumina carrier.

The amount of mixed metal oxide of alumina second component present in the carrier is typically at least about 0.01 weight % and up to about 20 weight % by weight of the carrier. In one embodiment, the mixed metal oxide of alumina second component is present in the carrier in a concentration of at least about 0.05 weight % and up to about 10 weight % of the carrier. In another embodiment, the mixed metal oxide of alumina second component is present in the carrier in a concentration of at least about 0.1 weight % and up to about 2 weight % of the carrier.

The amount of alumina first component present in the carrier is typically at least about 80 weight % and up to about 99.5 weight % of alumina by weight of the carrier. In one embodiment, the alumina first component is present in the carrier in a concentration of at least about 85 weight % and up to about 99 weight % of the carrier. In another embodiment, the alumina first component is present in the carrier in a concentration of at least about 90 weight % and up to about 99 weight % of the carrier.

The alumina first component of the carrier of the present disclosure is composed of any of the refractory alumina compositions known in the art for use in ethylene oxidation catalysts. In one embodiment of the present disclosure, the carriers include alpha-alumina as the alumina first component. The alpha-alumina used in the present disclosure typically has a very high purity, i.e., about 95 weight % or more, and more typically, 98 weight % or more alpha-alumina. A lower purity (80 weight % to 95 weight %) alpha alumina can also be used. Remaining components of the carrier of the present disclosure may be other phases of alumina, silica, mullite, alkali metal oxides (e.g., sodium oxide) and trace amounts of other metal-containing and/or non-metal-containing additives or impurities.

In one embodiment of the present disclosure, the carrier of the present disclosure including the mixed metal oxide of alumina second component is provided by forming the mixed metal oxide on a crystal surface of alumina particles that are used in forming an alumina powder which can be processed into a carrier. In this embodiment, a metal source, which serves as a 'mixed metal oxide of alumina precursor', is added to an alumina precursor and thereafter the admixture is fired, i.e., calcined, to form alumina particles that are coated with a mixed metal oxide of alumina. The terms "calcined" or "calcination" refer to a thermal treatment process applied to solid materials in order to bring about a thermal decomposition, phase transition, or removal of a volatile fraction; this is different from a drying step in which none of thermal decomposition, phase transition, or removal of a volatile fraction is achieved. The calcination process normally takes place at temperatures below the melting point of the product material. The adding step may include grinding and/or ball milling each of the precursors prior to, and/or after admixing.

The alumina precursor that can be employed in the present disclosure includes conventional materials that are well known in the art of carrier manufacturing. Illustrative examples of alumina precursors that can be employed in the present disclosure include, but are not limited to, hydrate alumina, i.e., Al trihydrate ($Al(OH)_3$), or pseudo-hydrate alumina, i.e., $Al_2O_3 \cdot nH_2O$, where $1<n>3$. Examples of various types of hydrate alumina that can be used include, for example, boehmite, gibbosite, bayersite, diaspore and mixtures thereof. In one embodiment, boehmite is employed as the alumina precursor.

In one embodiment, the metal source which can be used as the 'mixed metal oxide of alumina precursor' includes a metal salt such as, for example, M acetate ($CH_3COO^-$), M carbonate ($CO_3^{2-}$), M halide ($F^-$, $Br^-$, $Cl^-$, etc.), M citrate ($HOC(COO^-)(CH_2COO^-)$), M hydroxide ($OH^-$), M nitrate ($NO_3^-$), M nitrite ($NO_2^-$), M phosphate ($PO_4^{3-}$), or M sulfate ($SO_4^{2-}$), wherein M is as defined as one of the transition metals from the first row of the Periodic Table of Elements, i.e., one of Sc, Ti, V, Cr, Mn, Fe, Co, Ni, Zn Cu and Zn. In another embodiment, the metal source which can be used as the 'mixed metal oxide of alumina precursor' is a M oxide wherein M is one of Sc, Ti, V, Cr, Mn, Fe, Co, Ni, Zn Cu and Zn. In some embodiments, mixtures of the aforementioned metal sources can be employed. In one embodiment, chromium nitrate is employed as the metal source.

The concentration of the metal source added to the alumina precursor should be of a sufficient quantity to form a mixed metal oxide of alumina on the surface of the subsequently formed alumina particles upon firing the admixture. Typically, the concentration of the metal source that is employed in this embodiment of the present disclosure is from about 0.01 weight % to about 40 weight % based on 100 weight percent of the admixture. More typically, the concentration of the metal source that is employed in this embodiment of the present disclosure is from about 0.1 weight % to about 30 weight % based on 100 weight percent of the admixture.

The admixture of the metal source and the alumina precursor is then fired, i.e., calcined, at a sufficient high temperature to cause the in-situ formation of a mixed metal oxide of alumina component. The firing step is typically performed at a temperature from about 300° C. to about 2000° C., with a firing temperature from about 500° C. to about 1700° C. being more typical.

A suitable catalyst carrier can be prepared by combining the mixed metal oxide of alumina-containing alumina powder, a solvent such as water, a temporary binder, a permanent binder, and a porosity controlling agent, and then firing (i.e., calcining) the mixture by methods well known in the art. Optionally, the mixture may also include, colloidal silica, silicate salt or aluminum silicate.

Temporary binders, also function as burnout materials, include cellulose, substituted celluloses, e.g., methylcellulose, ethylcellulose, and carboxyethylcellulose, stearates (such as organic stearate esters, e.g., methyl or ethyl stearate), and waxes. Burnout material is used primarily to ensure the preservation of a porous structure during the green (i.e., unfired phase) in which the mixture may be shaped into particles by molding or extrusion processes. Burnout materials are essentially completely removed during the firing to produce the finished carrier. Examples of burnout materials include, for example, granulated polyolefins (e.g., polyethylene and polypropylene), graphite, walnut shell flour, and the like, which are decomposable at the calcination temperatures employed.

Permanent binders include, for example, inorganic clay-type materials, such as silica and an alkali metal compound. A convenient binder material which may be incorporated with the alumina particles is a mixture of boehmite, clay binder, stabilized silica sol, alkaline earth silicates, and/or a soluble sodium salt.

The formed paste is extruded or molded into a desired shape and fired at a temperature typically from about 1200° C. to about 1600° C. to form the carrier. Where the particles are formed by extrusion, it may be desirable to include conventional extrusion aids.

In another embodiment of the present disclosure, the mixed metal oxide of alumina-containing carrier can be prepared by combining a metal salt that serves as a 'mixed metal oxide of alumina precursor' with an alpha alumina powder, a solvent such as water, a temporary binder, a permanent binder, and a porosity controlling agent, and then firing (i.e., calcining) the mixture by methods well known in the art. During the firing step, the mixed metal oxide of alumina forms in-situ on the surface of the alumina carrier.

After providing an alpha alumina powder utilizing conventional techniques well known in the art, an admixture is provided that includes one of the above mentioned metal salts (i.e., M acetate ($CH_3COO^-$), M carbonate ($CO_3^{2-}$), M halide ($F^-$, $Br^-$, $Cl^-$, etc.), M citrate ($HOC(COO^-)(CH_2COO^-)$), M hydroxide ($OH^-$), M nitrate ($NO_3^-$), M nitrite ($NO_2^-$), M phosphate ($PO_4^{3-}$), or M sulfate ($SO_4^{2-}$), wherein M is as defined above), the alumina powder, a solvent such as water, a temporary binder, a permanent binder, and a porosity controlling agent, and thereafter the admixture is fired (i.e., calcined) by methods well known in the art.

The amount of metal salt employed in this embodiment of the present disclosure is generally lower than the amount of metal source mentioned in the previous embodiment of the present disclosure. Typically, the concentration of the metal salt that is employed in this embodiment of the present disclosure is from about 0.01 weight % to about 10 weight % based on 100 weight percent of the admixture.

The resultant paste which includes the metal salt is extruded or molded into a desired shape and fired at a temperature typically from about 1200° C. to about 1600° C. to form the mixed metal oxide of alumina-containing carrier.

During the firing step, the mixed metal oxide of alumina second component forms in-situ on the surface of the alumina carrier.

In yet another embodiment of the present disclosure, the carrier of the present disclosure including the mixed metal oxide of alumina second component can be obtained by first providing a preformed alumina carrier, soaking the same in a metal salt-containing solution which serves as the 'mixed metal oxide of alumina precursor', drying and then firing the dried and soaked preformed carrier to form the mixed metal oxide of alumina second component on the carrier's surface.

In this embodiment, a preformed alumina carrier is first provided using conventional methods that are well known to those skilled in the art including, for example, admixing alpha alumina powder, a solvent such as water, a temporary binder, a permanent binder, and/or a porosity controlling agent, and then firing (i.e., calcining) the mixture by methods well known in the art. See, the above general description regarding the formation of the carriers.

After firing the carrier, the preformed carrier is soaked in a solution which contains one of the above mentioned metal salts. The metal salt containing solution is prepared by admixing one of the above mentioned metal salts in a solvent that is capable of dissolving the metal salt, e.g., water.

The amount of metal salt added to the solvent is typically from about 0.01 weight % to about 20% weight % based on 100 ml of solvent, with an amount from about 0.1 weight % to about 10% weight % based on 100 ml of solvent being more typical.

The admixing and subsequent soak may be performed at room temperature (20° C.-40° C.) up to, but not beyond the boiling point of the solvent employed. The duration of the soak may vary depending on the shape and type of alumina carrier being subjected to this embodiment of the present disclosure. Typically, the soak is performed for a time period from about 1 minute to about 48 hours, with from about 15 minutes to about 5 hours, being more typical.

Following the soak step, the soaked preformed alumina carrier is removed from the solution and thereafter dried. The drying step can be performed at room temperature, up to, but not beyond 250° C. Typically, the drying step is performed at a temperature of about 70° C. to about 200° C. The duration of the drying step may vary. Typically, the duration of the drying step is within a range from about 15 minutes to about 48 hours, with from about 1 hour to about 24 hours, being more typical. Following the drying step, the dried and soaked preformed carrier is fired at a temperature which causes the formation of the mixed metal oxide of alumina on the surface of the preformed carrier. Typically, the firing step is performed within the ranges mentioned above for the other two embodiments of the present disclosure that form carrier of the present disclosure.

In most cases, the presence of mixed metal oxide of alumina component on the surface of the carrier may be detected by the characteristic color of the mixed oxide structure. For instance, a Cr-alumina mixed metal oxide is pink in color. The characteristic colors of the different mixed metal oxides of alumina are the result of the unique lattice arrangement which is stable and not subject to dissolution in common solvent, water for instance.

The formation of mixed metal oxides of alumina may be proven via surface analysis, e.g., X-ray powder diffraction analysis.

Notwithstanding which of the above mentioned techniques are employed in forming the carrier of the present disclosure, the carrier of the present disclosure is typically porous and has a B.E.T. surface area of at most 20 m$^2$/g. The B.E.T. surface area is more typically in the range of about 0.1 to 10 m$^2$/g, and more typically from 0.2 to 3 m$^2$/g. In other embodiments, the carriers of the present disclosure are characterized by having a B.E.T. surface area from about 0.3 m$^2$/g to about 3 m$^2$/g, preferably from about 0.5 m$^2$/g to about 2.5 m$^2$/g, and more preferably from about 0.6 m$^2$/g to about 2.0 m$^2$/g. The B.E.T. surface area described herein can be measured by any suitable method, but is more preferably obtained by the method described in Brunauer, S., et al., *J. Am. Chem. Soc.*, 60, 309-16 (1938).

The carrier of the present disclosure typically possesses a water absorption value ranging from about 0.2 cc/g to about 0.8 cc/g, and more typically from about 0.25 cc/g to about 0.6 cc/g.

The carrier of the present disclosure can have any suitable distribution of pore diameters. As used herein, the "pore diameter" is used interchangeably with "pore size". Typically, the pore diameters are at least about 0.01 microns (0.01 µm), and more typically, at least about 0.1 µm. In different embodiments, the pore diameters can be at least about 0.5 or 0.8 µm. Typically, the pore diameters are no more than about 50 µm.

The carrier of the present disclosure can be monomodal or multimodal such as, for example, bimodal. Without wishing to be bound by any theory, it is believed that a catalyst with a bimodal pore size distribution possesses a type of pore structure in which reaction chambers are separated by diffusion channels.

In one embodiment, at least 40% (and typically at least 60%, and more typically at least 80%) of the pore volume is due to pores with diameters between 1 and 5 micrometers. The median pore diameter of the carrier employed is typically between about 1 and 5 micrometers, more typically between about 1 and 4.5 micrometers, and even more typically between about 1 and 4 micrometers. The pore volume from pores with a diameter of 5 micrometers and above is typically less than about 0.20 ml/g, more typically less than about 0.10 ml/g, and even more typically less than about 0.05 ml/g. The pore volume from pores with a diameter of 1 micrometer and less is typically less than about 0.20 ml/g, more typically less than about 0.16 ml/g.

In some embodiments, the water pore volume can be from about 0.10 cc/g to about 0.80 cc/g, and more typically from about 0.20 cc/g to about 0.60 cc/g. The pore volume and pore size distribution described herein can be measured by any suitable method, but are more preferably obtained by the conventional mercury porosimeter method as described in, for example, Drake and Ritter, "Ind. Eng. Chem. Anal. Ed.," 17, 787 (1945).

The carrier of the present disclosure can be of any suitable shape or morphology. For example, the carrier can be in the form of particles, chunks, pellets, rings, spheres, three-holes, wagon wheels, cross-partitioned hollow cylinders, and the like, of a size preferably suitable for employment in fixed bed reactors. Typically, carrier particles have equivalent diameters in the range of from about 3 mm to about 12 mm, and more typically in the range of from about 5 mm to about 10 mm, which are usually compatible with the internal diameter of the tubular reactors in which the catalyst is placed. As known in the art, the term "equivalent diameter" is used to express the size of an irregularly-shaped object by expressing the size of the object in terms of the diameter of a sphere having the same volume as the irregularly-shaped object.

In another aspect, the present disclosure is directed to an ethylene epoxidation catalyst produced from the carrier described above. In order to produce the catalyst, a carrier having the above characteristics is then provided with a catalytically effective amount of silver thereon and/or therein. The catalyst can be prepared by impregnating the carrier of the present disclosure including the mixed metal oxide of alumina second component with silver ions, compounds, complexes, and/or salts dissolved in a suitable solvent sufficient to cause deposition of silver precursor compound onto and/or into the carrier. The carrier can be impregnated and incorporated with rhenium and silver, along with any desired promoters, by any of the conventional methods known in the art, e.g., by excess solution impregnation, incipient wetness impregnation, spray coating, and the like. Typically, the carrier material is placed in contact with the silver-containing solution until a sufficient amount of the solution is absorbed by the carrier. Infusion of the silver-containing solution into the carrier can be aided by application of a vacuum. A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

Silver compounds useful for impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. The silver solution used to impregnate the carrier can contain any suitable solvent. The solvent can be, for example, water-based, organic-based, or a combination thereof. The solvent can have any suitable degree of polarity, including highly polar, moderately polar or non-polar, or substantially or completely non-polar. The solvent typically has sufficient solvating power to solubilize the solution components. A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In one embodiment, the solution comprises an aqueous solution of silver oxalate and ethylene diamine. The complexing/solubilizing agent may be present in the impregnating solution in an amount from about 0.1 to about 10 moles of ethylene diamine per mole of silver, preferably from about 0.5 to about 5 moles, and more preferably from about 1 to about 4 moles of ethylene diamine for each mole of silver.

The concentration of silver salt in the solution is typically in the range from about 0.1% by weight to the maximum permitted by the solubility of the particular silver salt in the solubilizing agent employed. More typically, the concentration of silver salt is from about 0.5% to 45% by weight of silver, and even more typically, from about 5 to 35% by weight.

Any one or more promoting species in a promoting amount can be incorporated into the carrier either prior to, coincidentally with, or subsequent to the deposition of the silver. As used herein, a "promoting amount" of a certain component refers to an amount of that component that works effectively to provide an improvement in one or more of the catalytic properties of a subsequently formed catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity.

For example, catalysts that are based on the carrier described above may include a promoting amount of an alkali metal or a mixture of two or more alkali metals. Suitable alkali metal promoters include, for example, lithium, sodium, potassium, rubidium, cesium or combinations thereof. In one embodiment, cesium can be employed. In another embodiment, combinations of cesium with other alkali metals can be employed. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the alkali metal.

The catalyst that is based on carrier of the present disclosure may also include a promoting amount of a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The catalyst that is based on the carrier of the present disclosure may also include a promoting amount of a main group element or a mixture of two or more main group elements. Suitable main group elements include any of the elements in Groups IIIA (boron group) to VIIA (halogen group) of the Periodic Table of the Elements. For example, the carrier can include a promoting amount of one or more sulfur compounds, one or more phosphorus compounds, one or more boron compounds, one or more halogen-containing compounds, or combinations thereof. The carrier can also include a main group element, aside from the halogens, in its elemental form.

The catalyst that is based on the carrier of the present disclosure may also include a promoting amount of a transition metal or a mixture of two or more transition metals. Suitable transition metals can include, for example, the elements from Groups IIIB (scandium group), IVB (titanium group), VB (vanadium group), VIB (chromium group), VIIB (manganese group), VIIIB (iron, cobalt, nickel groups), IB (copper group), and IIB (zinc group) of the Periodic Table of the Elements, as well as combinations thereof. More typically, the transition metal is an early transition metal, i.e., from Groups IIIB, IVB, VB or VIB, such as, for example, hafnium, yttrium, molybdenum, tungsten, rhenium, chromium, titanium, zirconium, vanadium, tantalum, niobium, or a combination thereof.

In one embodiment, the one or more promoters comprise an alkali metal. In another embodiment, the promoter includes Re and one or more species selected from Cs, K, Li, W, and S. In a further embodiment, the promoter includes Re and one or more species selected from Cs, Li, and S.

The catalyst that includes the carrier of the present disclosure may also include a promoting amount of a rare earth metal or a mixture of two or more rare earth metals.

The rare earth metals include any of the elements having an atomic number of 57-103. Some examples of these elements include lanthanum (La), cerium (Ce), and samarium (Sm).

The transition metal or rare earth metal promoters are typically present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal.

All of these promoters, aside from the alkali metals, can be in any suitable form, including, for example, as zerovalent metals or higher valent metal ions.

After impregnation with silver and any promoters, the impregnated carrier is removed from the solution and calcined for a time sufficient to reduce the silver component to metallic silver and to remove volatile decomposition products from the silver-containing support. The calcination is typically accomplished by heating the impregnated carrier, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods have been described in the art for the thermal treatment of impregnated supports.

During calcination, the impregnated support is typically exposed to a gas atmosphere comprising air or an inert gas, such as nitrogen. The inert gas may also include a reducing agent.

In another aspect, the present disclosure is directed to a method for the vapor phase production of ethylene oxide by conversion of ethylene to ethylene oxide in the presence of oxygen by use of the catalyst described above. Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. A typical process for the oxidation of ethylene to ethylene oxide comprises the vapor phase oxidation of ethylene with molecular oxygen in the presence of the catalyst of the present disclosure in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

The catalysts containing the carrier of the present disclosure have been shown to be particularly selective catalysts in the oxidation of ethylene with molecular oxygen to ethylene oxide. Selectivity values of at least about 83 mol % up to about 93 mol % are typically achieved. In some embodiments, the selectivity is from about 87 mol % to about 93 mole %. The conditions for carrying out such an oxidation reaction in the presence of the catalyst of the present disclosure broadly comprise those described in the prior art. This applies, for example, to suitable temperatures, pressures, residence times, diluent materials (e.g., nitrogen, carbon dioxide, steam, argon, and methane), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide.

The catalyst of the present disclosure can also exhibit increased crush strength and attrition resistance as compared to an equivalent ethylene oxide catalyst that is present on a carrier which is otherwise identical to the carrier of the present disclosure except that the carrier does not include the metal oxide of alumina second component of the present disclosure. Typically, the catalyst including the carrier of the present disclosure has a 10% or greater increase in crush strength as compared to an equivalent catalyst. The crush strength of the catalyst can be determined using standard testing methods such as, for example, ASTM D6175-03 (2008). The catalyst including the carrier of the present disclosure has a 10% or greater increase in attrition resistance as compared to an equivalent catalyst. The attrition resistance of the catalyst can be determined using standard methods such as, for example, ASTM D4058-96(2011)e1.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or by-products, unreacted materials are typically returned to the oxidation reactor. For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production (work rate) of 100-400 kg EO per cubic meters of catalyst per hour. More typically, the feed composition at the reactor inlet comprises 1-40% ethylene, 3-12% oxygen, 0.3-40% $CO_2$, 0-3% ethane, 0.3-20 ppmv total concentration of organic chloride moderator, and the balance of the feed comprised of argon, methane, nitrogen, or mixtures thereof.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, and the balance nitrogen.

The resulting ethylene oxide is separated and recovered from the reaction products using methods known in the art. The ethylene oxide process may include a gas recycle process wherein a portion or substantially all of the reactor effluent is readmitted to the reactor inlet after substantially removing the ethylene oxide product and byproducts. In the recycle mode, carbon dioxide concentrations in the gas inlet to the reactor may be, for example, from about 0.3 to about 6, preferably from about 0.3 to about 2.0, volume percent.

While there have been shown and described what are presently believed to be the preferred embodiments of the present disclosure, those skilled in the art will realize that other and further embodiments can be made without departing from the spirit and scope of the present disclosure, and this disclosure includes all such modifications that are within the intended scope of the claims set forth herein.

The following non-limiting examples serve to illustrate the invention.

Example 1

Carrier preparation: Boehmite alumina was mixed with a water solution containing chromium oxide. The resultant paste was dried and then calcined by heating gradually up to 1000° C. for 4 hours to produce alpha alumina crystals that have a surface area of 2 m$^2$/g. The alpha alumina was mixed with 10% of untreated boehmite, ceramic binding agent, 5% extrusion aid (Vaseline) and enough water to form an extrudable paste. After mixing and ageing for 24 hours, the paste was extruded and cut to produce a pelletized "green ware". The extruded pellets were dried for 2 hours at 150° C. and then placed in a calcination oven. The temperature of the oven was ramped at the rate of 250° C. per hours up to 1500° C. The temperature was maintained at this temperature for 8 hours and then cooling started at a rate of 250° C. per hour until it reached 25° C., to produce carrier I. The carrier produced was characterized by a pale purple color and contained 0.06% Cr. The physical properties of the carrier are listed in Table 1.

Example 2

Comparative Example

The same procedure of Example 1 was followed except there was no chromium compound added, to produce carrier II. The carrier produced was characterized by its typical clear white color. The physical properties of the carrier are listed in table 1

TABLE 1

|  | Carrier II | Carrier I |
| --- | --- | --- |
| Surface area m$^2$/g | 0.64 | 0.88 |
| Crush strength lb | 11.1 | 19.6 |
| Water absorption ml/g | 0.53 | 0.5 |

Example 3

An alpha alumina powder of surface area 1.8 m$^2$/g was mixed with a diluted water solution of chromic acid, 10% of boehmite, 5% colloidal silica, 5% extrusion aid (Vaseline) and enough water to form an extrudable paste. After mixing and ageing for 24 hours, the paste was extruded and cut to produce a pelletized "green ware". The extruded pellets were dried for 2 hours at 150° C. and then placed in a calcination oven. The temperature of the oven was ramped at the rate of 250° C. per hours up to 1400° C. The temperature was maintained at this temperature for 9 hours and then cooling started at a rate of 250° C. per hour until it reached 25° C., to produce carrier III. The carrier produced was characterized by its purple color and contained 0.1% Cr. The physical properties of the carrier are listed in Table 2.

Example 4

The same procedure of Example 3 was followed except the chromium solution was replaced with a solution of titanium bis-ammonium lactato dihydroxide. The carrier produced was characterized by its white color and contained 0.2% Ti, carrier IV. The physical properties of the carrier are listed in Table 2.

Example 5

The same procedure of Example 3 was followed except the chromium solution was replaced with TiO$_2$ powder. The carrier produced was characterized by its white color and contained 0.3% Ti, carrier V. The physical properties of the carrier are listed in Table 2.

Example 6

Comparative Example

The same procedure of Example 3 was followed except the chromium solution was eliminated. The carrier produced was characterized by its white color and contained 0.2% Ti, carrier VI. The physical properties of the carrier are listed in Table 2.

TABLE 2

| Sample | Water absorption % | Attrition loss % | BET surface area m$^2$/g |
| --- | --- | --- | --- |
| Carrier III | 42.2 | 15 | 0.82 |
| Carrier IV | 43.6 | 14.8 | 0.7 |
| Carrier V | 44.4 | 18.8 | 0.74 |
| Carrier VI (comparative) | 43 | 22 | 0.74 |

Example 7

Catalyst Preparation

Silver based catalyst preparation and activation followed generally conventional procedures, as disclosed above. Specifically, a 300 g portion of the alumina support was placed in a flask and evacuated to about 0.1 torr prior to impregnation. To the above silver solution were added aqueous solutions of cesium hydroxide, perrhenic acid, and ammonium sulfate in order to prepare a catalyst composition according to examples 5-10 of U.S. Pat. No. 4,766,105 to Lauritzen et al. After thorough mixing, the promoted silver solution was aspirated into the evacuated flask to cover the carrier while maintaining the pressure at about 0.1 torr. The vacuum was released after about 5 minutes to restore ambient pressure, hastening complete penetration of the solution into the pores. Subsequently, the excess impregnation solution was drained from the impregnated carrier.

Calcination of the wet catalyst was performed on a moving belt calciner. In this unit, the wet catalyst was transported on a stainless steel belt through a multi-zone furnace. All zones of the furnace were continuously purged with pre-heated, nitrogen and the temperature was increased gradually as the catalyst passed from one zone to the next. The heat supplied to the catalyst was radiated from the furnace walls and from the preheated nitrogen. In this example, the wet catalyst entered the furnace at ambient temperature. The temperature was then increased gradually to a maximum of about 450° C. as the catalyst passed through the heated zones. In the last (cooling) zone, the temperature of the now calcined catalyst was immediately lowered to less than 100° C. before it emerged into ambient atmosphere. The total residence time in the furnace was approximately 45 minutes.

Example 8

Catalyst Testing

The catalysts were subjected to an accelerated ageing test, in order to illustrate the enhanced stability of the instant invention. The silver based catalyst, crushed, sieved, and charged into 8 mm reactor tube and was tested with a feed gas mixture that included the following components: 10% ethylene; 4% oxygen; 2% carbon dioxide; 0.8 parts per million, ethyl chloride (moderator); and balance nitrogen.

The temperature of the reactor was increased gradually up to 245° C. while allowing the carbon dioxide to be increased to 8%. After 100 hours, the carbon dioxide concentration in the feed was lowered to 6% in order to maintain the concentration of ethylene oxide in the effluent at 2.2%. After an additional forty hours of heating at 247° C., the selectivity was 84.0% and the effluent gas contained 2.5% ethylene oxide.

The catalyst was cooled down to 220° C. and then the feed composition was gradually adjusted to the accelerated ageing test and the temperature was increased to achieve 2.5% ethylene oxide in the effluent, using the following mixture: 15% ethylene; 7% oxygen; 2% carbon dioxide; 1.5 parts per million, ethyl chloride (moderator); and balance nitrogen.

Under the aforementioned conditions, the catalyst's performance was: 88.5% selectivity; 2.5% ethylene oxide in the effluent; and Vol. work rate 450 kg/m$^3$/hr.

The results of testing the different catalysts are summarized in Table III.

TABLE III

| Catalyst | Carrier | Selectivity decline rate (relative to the comparative carrier) |
| --- | --- | --- |
| 1 | I | 0.2 |
| 2 | II | 1 |
| 3 | III | 0.3 |
| 4 | IV | 0.35 |
| 5 | V | 0.27 |
| 6 | VI | 1 |

While the present disclosure has been particularly shown and described with respect to various embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A carrier for an ethylene epoxidation catalyst, the carrier comprising an alumina first component, and a mixed metal oxide of alumina second component, wherein said mixed metal oxide of alumina second component comprises a corundum lattice structure having a plurality of O—Al—O bonds, wherein an Al atom of at least one O—Al—O bond of the plurality of O—Al—O bonds, but not all of the plurality of O—Al—O bonds, is replaced with a divalent or trivalent transition metal selected from the group consisting of scandium (Sc), titanium (Ti), vanadium (V), chromium (Cr), manganese (Mn), iron (Fe), cobalt (Co), nickel (Ni) copper (Cu), and zinc (Zn).

2. The carrier of claim 1, wherein the alumina first component is alpha-alumina.

3. The carrier of claim 1, wherein the mixed metal oxide of alumina second component is present in a concentration from about 0.01 weight % to about 20 weight %.

4. The carrier of claim 1, wherein said transition metal is selected from the group consisting of Cr, Co, Mn, and Ni.

5. The carrier of claim 1, wherein said transition metal is Cr.

6. The carrier of claim 1, wherein said mixed metal oxide of alumina second component coats a surface of said alumina first component.

7. The carrier of claim 1, further comprising a promoting amount of an alkali or alkaline earth metal.

8. The carrier of claim 1, further comprising a promoting amount of cesium.

9. An ethylene epoxidation catalyst comprising:
a carrier comprising an alumina first component and a mixed metal oxide of alumina second component, wherein said mixed metal oxide of alumina second component comprises a corundum lattice structure having a plurality of O—Al—O bonds, wherein an Al atom of at least one O—Al—O bond of the plurality of O—Al—O bonds, but not all of the plurality of O—Al—O bonds, is replaced with a divalent or trivalent transition metal selected from the group consisting of scandium (Sc), titanium (Ti), vanadium (V), chromium (Cr), manganese (Mn), iron (Fe), cobalt (Co), nickel (Ni) copper (Cu), and zinc (Zn);
a catalytic amount of silver deposited on and/or in said carrier; and
a promoting amount of one or more promoters deposited on and/or in said carrier.

10. The catalyst of claim 9, wherein the one or more promoters is cesium.

11. The catalyst of claim 9, wherein the one or more promoters is potassium.

12. The catalyst of claim 9, wherein the one or more promoters is rhenium.

13. The catalyst of claim 12, further comprising a promoting amount of an alkali or alkaline earth metal.

14. The catalyst of claim 12, further comprising a promoting amount of potassium.

15. The catalyst of claim 12, further comprising a promoting amount of cesium.

16. The catalyst of claim 12, further comprising a promoting amount of tungsten.

17. The catalyst of claim 12, further comprising a promoting amount of sulfur.

18. The catalyst of claim 12, further comprising a promoting amount of cesium, lithium, tungsten, and sulfur.

19. The catalyst of claim 12, further comprising a promoting amount of cesium, lithium, and sulfur.

20. The catalyst of claim 9, wherein the alumina first component is alpha-alumina.

21. The catalyst of claim 9, wherein the mixed metal oxide of alumina second component is present in a concentration from about 0.01 weight % to about 20 weight %.

22. The catalyst of claim 9, wherein said transition metal is selected from the group consisting of Cr, Co, Mn, and Ni.

23. The catalyst of claim 9, wherein said transition metal is Cr.

24. The catalyst of claim 9, wherein said mixed metal oxide of alumina second component coats a surface of said alumina first component.

25. A method for the vapor phase conversion of ethylene to ethylene oxide in the presence of oxygen, the method comprising reacting a reaction mixture comprising ethylene and oxygen in the presence of a catalyst, said catalyst comprising:

a carrier comprising an alumina first component and a mixed metal oxide of alumina second component, wherein said mixed metal oxide of alumina second component comprises a corundum lattice structure having a plurality of O—Al—O bonds, wherein an Al atom of at least one O—Al—O bond of the plurality of O—Al—O bonds, but not all of the plurality of O—Al—O bonds, is replaced with a divalent or trivalent transition metal selected from the group consisting of scandium (Sc), titanium (Ti), vanadium (V), chromium (Cr), manganese (Mn), iron (Fe), cobalt (Co), nickel (Ni) copper (Cu), and zinc (Zn);

a catalytic amount of silver deposited on and/or in said carrier; and a promoting amount of one or more promoters deposited on and/or in said carrier.

26. The method of claim 25, wherein the alumina first component is alpha-alumina.

27. The method of claim 25, wherein the mixed metal oxide of alumina second component is present in a concentration from about 0.01 weight % to about 20 weight %.

28. The method of claim 25, wherein said transition metal is selected from the group consisting of Cr, Co, Mn, and Ni.

29. The method of claim 25, wherein said transition metal is Cr.

30. The method of claim 25, wherein said mixed metal oxide of alumina second component coats a surface of said alumina first component.

31. The method of claim 25, wherein said one or more promoters comprise rhenium.

32. The method of claim 31, further comprising a promoting amount of an alkali or alkaline earth metal.

33. The method of claim 31, further comprising a promoting amount of cesium.

34. The method of claim 31, further comprising a promoting amount of tungsten.

35. The method of claim 31, further comprising a promoting amount of sulfur.

36. The method of claim 31, further comprising a promoting amount of cesium, lithium, tungsten, and sulfur.

37. The method of claim 31, further comprising a promoting amount of cesium, lithium, and sulfur.

38. A method of making a carrier, said method comprising:

admixing an alumina precursor with a mixed metal oxide of alumina precursor; and calcining the admixture at a temperature to form alumina particles which are coated with a mixed metal oxide of alumina, wherein said mixed metal oxide of alumina comprises a corundum lattice structure having a plurality of O—Al—O bonds, wherein an Al atom of at least one O—Al—O bond of the plurality of O—Al—O bonds, but not all of the plurality of O—Al—O bonds, is replaced with a divalent or trivalent transition metal selected from the group consisting of scandium (Sc), titanium (Ti), vanadium (V), chromium (Cr), manganese (Mn), iron (Fe), cobalt (Co), nickel (Ni) copper (Cu), and zinc (Zn).

39. The method of claim 38, further comprising incorporating a catalytic amount of silver, and a promoting amount of one or more promoters into said carrier.

40. A method of making a carrier, said method comprising:

providing a preformed alumina carrier;

soaking said preformed alumina carrier in a solution comprising a mixed metal oxide of alumina precursor;

drying the soaked preformed alumina carrier; and calcining the dried and soaked preformed alumina carrier at a temperature to form a alumina carrier comprising a mixed metal oxide of alumina component, wherein said mixed metal oxide of alumina component comprises a corundum lattice structure having a plurality of O—Al—O bonds, wherein an Al atom of at least one O—Al—O bond of the plurality of O—Al—O bonds, but not all of the plurality of O—Al—O bonds, is replaced with a divalent or trivalent transition metal selected from the group consisting of scandium (Sc), titanium (Ti), vanadium (V), chromium (Cr), manganese (Mn), iron (Fe), cobalt (Co), nickel (Ni) copper (Cu), and zinc (Zn).

41. The method of claim 40, further comprising incorporating a catalytic amount of silver, and a promoting amount of one or more promoters into said carrier.

42. A method of making a carrier, said method comprising:

combining a mixed metal oxide of alumina precursor with at least an alumina powder and a solvent to form a paste;

forming said paste into a desired shape; and calcining the shaped paste at a temperature to form a carrier containing a mixed metal oxide of alumina component, wherein said mixed metal oxide of alumina component comprises a corundum lattice structure having a plurality of O—Al—O bonds, wherein an Al atom of at least one O—Al—O bond of the plurality of O—Al—O bonds, but not all of the plurality of O—Al—O bonds, is replaced with a divalent or trivalent transition metal selected from the group consisting of scandium (Sc), titanium (Ti), vanadium (V), chromium (Cr), manganese (Mn), iron (Fe), cobalt (Co), nickel (Ni) copper (Cu), and zinc (Zn).

43. The method of claim 42, further comprising incorporating a catalytic amount of silver, and a promoting amount of one or more promoters into said carrier.

* * * * *